April 8, 1952 E. G. FISHER Plant Pat. 1,081
HYBRID TEA ROSE PLANT
Filed Feb. 15, 1950
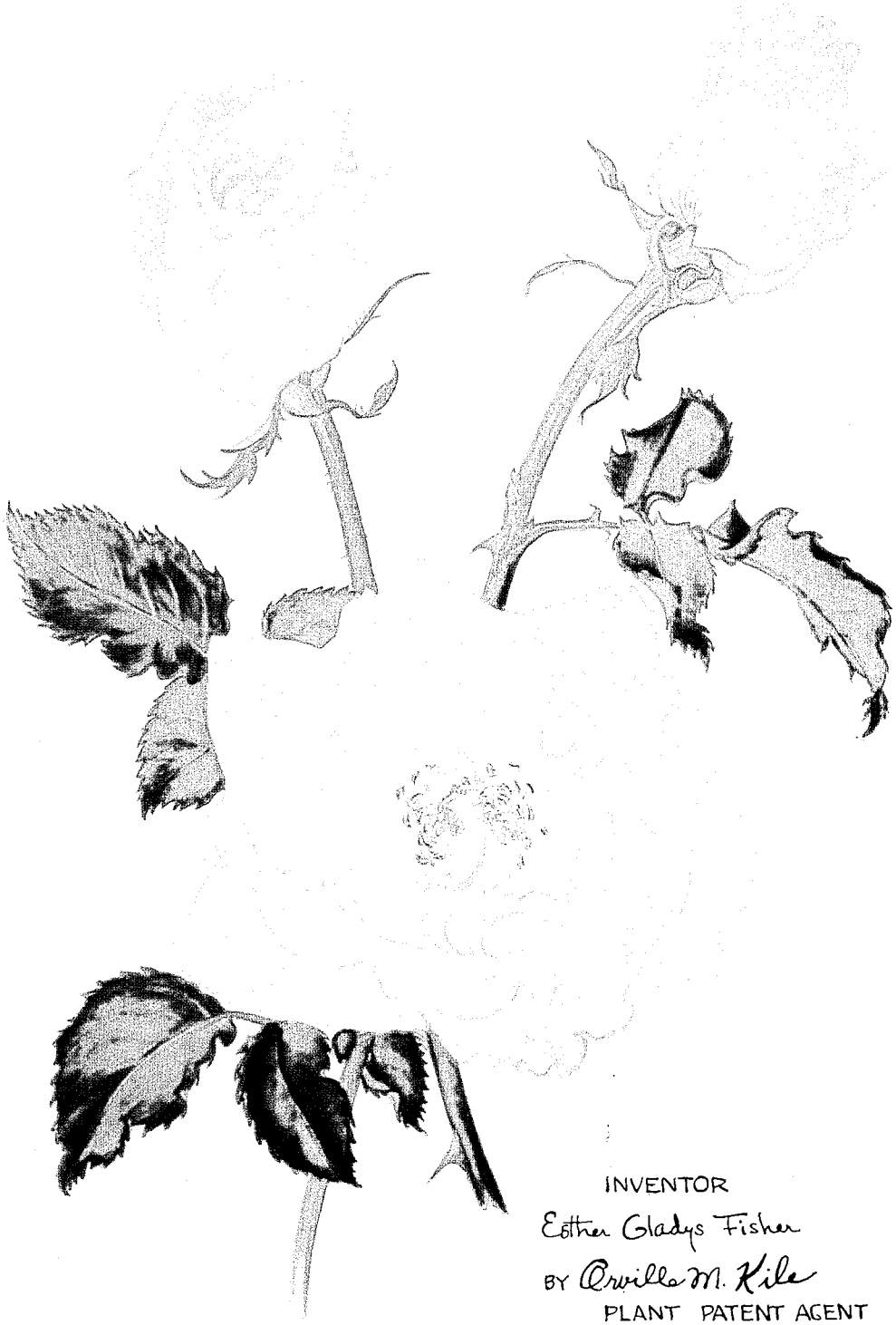
INVENTOR
Esther Gladys Fisher
BY Orville M. Kile
PLANT PATENT AGENT Patented Apr. 8, 1952

Plant Pat. 1,081

UNITED STATES PATENT OFFICE 1,081

HYBRID TEA ROSE PLANT

Esther Gladys Fisher, Woburn, Mass., assignor to Arnold-Fisher Company, Woburn, Mass.

Application February 15, 1950, Serial No. 144,215

1 Claim. (Cl. 47—61)

My present invention relates to a new and improved variety of hybrid tea rose plant which resulted from a cross made by me in our greenhouses at Woburn, Massachusetts. The female parent was Talisman (unpatented) and the male parent R. M. S. Queen Mary (Plant Patent No. 249).

This new variety is primarily a garden rose, producing many flowers throughout the entire season from early spring to late fall. Although its growth looks somewhat like that of Talisman—one of its parents—it is deceptive in that it has much greater strength of growth and stem, this strength being one of its outstanding characteristics, apparently inherited from its other parent—R. M. S. Queen Mary. Its flower shows characteristics of both of its parents in its form and coloring, being well-formed and high centered with a combination of salmon, pink and orange-yellow in its coloring.

This new variety has been reproduced by means of budding, in our greenhouses and gardens at Woburn, Massachusetts, and its characteristics appear to be permanent.

The accompanying illustrations show, in approximately true colors, three specimens of the flower of my new variety as produced in the late fall. It must be understood, however, that there is considerable variation between specimens in the amounts and tone of the colors, and that in the spring the flowers show a much greater proportion of golden orange.

In the following detailed description, color plate numbers refer to Ridgway's Color Standards and Nomenclature. Where no plate number is given, the ordinary dictionary meaning is intended.

*The plant*

Form: Tall, compact bush, growing to a height of 4 or 4½ feet.

Growth: Strong and wiry. Free-branching. Talisman-like in appearance but a very much stronger grower.

Blooming habit: In the garden it is a continuous bloomer from early spring to late fall in this climate, and is covered with many buds at all times.

Foliage: Leaflets 1 to 5.

*Size.*—Small to medium. The terminal leaflet averages about 2 inches long and 1½ inches wide.

*Quantity.*—Moderate.

*Shape.*—Broadly oval with rounded base. Edge sharply and shallowly serrated.

*Color.*—Dark Dull Yellow Green (Plate XXXII) on the upper surface. Approximately Light Hellebore Green (Plate XVII) on the under surface. Sometimes the leaves are edged with red. New shoots are green in summer, red in fall.

*Texture.*—Leathery; smooth.

*Rachis.*—Red; grooved on upper surface. Under side smooth except for a prickle or two.

*Stipules.*—Narrow; long; clinging.

Stems:

*Color.*—Olive green, mostly covered with an overlay of reddish brown.

*Size.*—Large and sturdy. Flower stems long.

*Thorns.*—Large; sharp-pointed; red; pointing at right angles to stem.

Disease resistance: Variety appears to be entirely free of common rose diseases.

*The flower*

Bud:

*Size.*—Large.

*Form.*—Pointed, opening to urnshape.

*Color.*—Fall flower buds approximately Geranium Pink (Plate I), with splotches and aiglet of deep yellow. Inner petals of opening bud almost Rose Doree (Plate I). The spring flower buds are almost entirely golden orange, from Buff Yellow (Pl. IV) to Capucine Yellow (Pl. III).

*Sepals.*—Foliaceous; reflex early.

*Peduncle.*—Short; sturdy; strong; same color as stems.

Bloom:

*Borne.*—Singly on long sturdy stems.

*Size.*—Large, approximately 5 inches in diameter.

*Form.*—High-centered, opening into a deep, loose cupshape and later flattening a little to reveal large number of pistils and stamens.

*Color.*—The fall flowers exhibit a combination of shades of salmon, orange-yellow and pink, varying considerably in various specimens as to the predominance of pink or of yellow tints, covering a range from Shrimp Pink to Rose Doree (Pl. I) and the orange-yellows from Buff Yellow (Pl. IV) to Capucine Orange (Pl. III). The inside petals are somewhat lighter in tone than the bud colors, and the fully opened flower is a combination of pink, salmon and yellow in tints still lighter. The spring flowers contain a much greater proportion of orange or gold and sometimes lack entirely the pink shadings, particularly in the bud stage.

*Petalage.*—About 25 petals as an average.

*Fragrance.*—Mild and pleasant.

*Longevity.*—Flowers last very well.

Petals:

*Shape.*—Outer petals almost round, cupped rather deeply near base. Inner petals smaller and central petals informally crinkled.

*Aspect.*—Smooth.

*Size.*—Outer petals are about 2½ inches in each direction.

*Persistence.*—Petals cling for a long time, then drop cleanly.

*Texture.*—Substantial but not heavy.

*Arrangement.*—Loose and informal.

Reproductive organs:

*Pistils.*—Many; tightly bunched. *Styles*—short and white. *Stigmas*—white or light yellow.

*Stamens.*—Many, surrounding pistils. *Filaments*—very light yellow and of uneven lengths. *Anthers*—large; dark brownish-yellow, mostly turning very dark before the petals fall.

*Comparisons*

The rose most like my nev variety is Mrs. Sam McGredy (unpatented)), but they differ principally as follows:

1. My rose is a brighter orange color, especially the springtime blooms.
2. The bush of my variety is much more compact, Mrs. Sam McGredy being much thinner and more scraggly.
3. My new variety is a taller grower.
4. My rose has longer flower stems.
5. My variety is a much better bloomer, producing more flowers.

Another variety which has been cited as somewhat similar to my new variety is the Hiscox rose, subject of Plant Patent No. 208. Chief differences are as follows:

1. The plant of my variety is more free-branching and compact in growth.
2. Stems of my variety are wiry as well as strong, whereas those of No. 208 are stiff.
3. Foliage of my variety is considerably darker in color and leaves are somewhat larger.
4. My variety produces more good flowers in a season.
5. The flower and bud colors vary in my variety with the seasons and are in lighter, softer tones and less spotty than those of No. 208.
6. Petals of my new variety are of lighter texture and are arranged more informally.
7. My new variety's flower is definitely not bi-color but is a soft suffusion of various tones of orange and Rose Doree to Shrimp Pink, while No. 208 may be called a bi-color in its later stages of opening.
8. My new variety is particularly disease-resistant and particularly adapted to outdoor culture, whereas No. 208 does not appear to be outstanding in these respects.

Having thus disclosed my invention, I claim:

The new and distinct variety of hybrid tea rose plant, substantially as herein shown and described, characterized particularly by its adaptability to garden culture; its compact growth of Talisman type in appearance but with much greater strength and vigor; its continuous blooming habit; its strong, wiry and long flower stems; its disease resistance; and its flowers in varying combination of shades of salmon, yellow-orange and pink, lightening considerably when the flower ages.

ESTHER GLADYS FISHER.

REFERENCES CITED

The following references are of record in the file of this patent:

UNITED STATES PATENTS

| Number | Name | Date |
|---|---|---|
| Pl. Pt. 208 | Hiscox | Nov. 24, 1936 |